United States Patent
Chen et al.

(10) Patent No.: US 12,215,084 B2
(45) Date of Patent: *Feb. 4, 2025

(54) 2(1H)-PYRIDINONES AND THEIR USE TO TREAT INFLAMMATORY CONDITIONS

(71) Applicant: Conopco, Inc., Englewood Cliffs, NJ (US)

(72) Inventors: Guoqiang Chen, Shanghai (CN); Yudong Wang, Shanghai (CN); Dandan Huang, Shanghai (CN)

(73) Assignee: Conopco, Inc., Englewood Cliffs, NJ (US)

(*) Notice: Subject to any disclaimer, the term of this patent is extended or adjusted under 35 U.S.C. 154(b) by 614 days.

This patent is subject to a terminal disclaimer.

(21) Appl. No.: 17/610,242

(22) PCT Filed: Apr. 30, 2020

(86) PCT No.: PCT/EP2020/062130
§ 371 (c)(1),
(2) Date: Nov. 10, 2021

(87) PCT Pub. No.: WO2020/229199
PCT Pub. Date: Nov. 19, 2020

(65) Prior Publication Data
US 2022/0242824 A1    Aug. 4, 2022

(30) Foreign Application Priority Data

May 14, 2019   (WO) ............... PCT/CN2019/086910
Jun. 17, 2019   (EP) ................................... 19180529

(51) Int. Cl.
| | |
|---|---|
| C07D 213/64 | (2006.01) |
| A61K 8/49 | (2006.01) |
| A61Q 5/00 | (2006.01) |
| A61Q 5/02 | (2006.01) |
| A61Q 5/12 | (2006.01) |

(52) U.S. Cl.
CPC .......... *C07D 213/64* (2013.01); *A61K 8/4926* (2013.01); *A61Q 5/006* (2013.01); *A61Q 5/02* (2013.01); *A61Q 5/12* (2013.01); *A61K 2800/81* (2013.01)

(58) Field of Classification Search
CPC .. A61K 8/4926; A61K 2800/81; A61Q 5/006; A61Q 5/02; A61Q 5/12; C07D 213/64
See application file for complete search history.

(56) References Cited

U.S. PATENT DOCUMENTS

| | | |
|---|---|---|
| 3,644,626 A | 2/1972 | Witzel |
| 3,655,897 A | 4/1972 | Witzel |
| 3,754,088 A | 8/1973 | Witzel |
| 4,451,469 A | 5/1984 | Singh et al. |
| 4,540,699 A | 9/1985 | Brown et al. |
| 7,547,752 B2 | 6/2009 | Bailey et al. |
| 11,826,453 B2* | 11/2023 | Chen ................. A61Q 5/12 |
| 2006/0165616 A1 | 7/2006 | Brock et al. |
| 2016/0128944 A1 | 5/2016 | Chawrai et al. |
| 2016/0310393 A1 | 10/2016 | Chang et al. |

FOREIGN PATENT DOCUMENTS

| | | | |
|---|---|---|---|
| CN | 103442681 | 12/2013 | |
| CN | 105748376 | 7/2016 | |
| CN | 106832439 | 6/2017 | |
| CN | 107875030 | 4/2018 | |
| DE | 102007045241 | 10/2008 | |
| EP | 0034385 | 8/1981 | |
| EP | 0173259 | 3/1986 | |
| EP | 1523298 | 4/2005 | |
| JP | 63179813 | 7/1988 | |
| JP | 2013253028 A | * 12/2013 | ............... A61Q 7/00 |

(Continued)

OTHER PUBLICATIONS

Gagliardi, L., et al.; "HPLC Determination of Ciclopirox, Octopirox, and Pyrithiones in Pharmaceuticals and Antidandruff Preparations"; Journal of Liquid Chromatography & Related Technologies; 21(15); pp. 2365-2373; 1998.

(Continued)

*Primary Examiner* — Blessing M Fubara
(74) *Attorney, Agent, or Firm* — Stephanie S. DelPonte

(57) ABSTRACT

Disclosed is a novel compound and a process of preparing it. It has been shown to have anti-inflammatory activity and can be utilised in a wide range of cosmetic compositions. The compound is a 2(1H)-pyridinone of formula (1) in amide or enol form. It may be prepared by exposing a solution of piroctone olamine in an organic solvent or in water comprising at least one surfactant to UV radiation to degrade the piroctone olamine. The compound of formula (1) is separated from the degradation products by chromatography.

Formula (1)

A: amide form         B: enol form

11 Claims, No Drawings

(56) References Cited

FOREIGN PATENT DOCUMENTS

| JP | 2016523232 | 8/2016 |
|---|---|---|
| JP | 2018511638 | 4/2018 |
| RU | 2324469 | 5/2008 |
| WO | WO9966886 | 12/1999 |
| WO | WO0067699 | 11/2000 |
| WO | WO2005041907 | 5/2005 |
| WO | WO2012022552 | 2/2012 |
| WO | WO2016058837 | 4/2016 |
| WO | WO2017184752 | 10/2017 |
| WO | WO2018172121 | 9/2018 |

OTHER PUBLICATIONS

Zhang, Q.; "Detection method of common anti-dandruff agent in cosmetics"; China Pharmaceuticals; 23(20); pp. 122-123; 2014.
Search Report and Written Opinoin in EP19180529; Nov. 21, 2019.
Gilbert A Youngdale et al; 1,2-Dihydro-2-oxo-6-(2,2-dimethylpropyl) 3-pyridinecarboxylic acid, "A new class of oral hypoglycemic agents" Analogues, and derivatives; J. Med. Chem; Jan. 1, 1985; 1790-1796 (also as XP055638504); 28.
Search Report and Written Opinoin in EP19180528; Nov. 21, 2019.
Streith Jacques et al: Bulletin De La Societe Chimique De France, Societe Francaise De Chimie. Paris, France, ; XP009516933; Reactions photoinduites de N-oxydes d'heterocycles aromatiques azotes IV (1,2,3), photochimie des pyridine-N-oxydes (4). [Photoreactions of aromatic nitrogenous heterocycle n-oxide]; Jan. 1, 1970; 1164, 1165; France. With machine translation of title and abstract.
J Streith et al; XP055639159; Tetrahedron Letters; Jan. 1, 1966; 1348, 1349. With machine translation of title and first paragraph.
Spec-Chem Ind; XP055625058; Spec-Chem Ind: "Pirontone Olamine"; Sep. 23, 2009; 3,6,8; www.in-cosmetics.com/_novadoc uments/ 2882.
Clariant; Antidandruff Active Ingredient Octopirox, Salzbach; XP055319009; Jun. 11, 2015; 9,13,14; www.myskinrecipes.com/shop/atta.
Search Report and Written Opinion in PCTEP2020062230; Jul. 29, 2020.
Search Report and Written Opinion in PCTEP2020062130; Jul. 29, 2020.
Streith, J., et al.; Reactions photoinduites de N-oxydes d'heterocycles aromatiques azotes IV (1,2,3), photochimie des pyridine-N-oxydes (4). [Photoreactions of aromatic nitrogenous heterocycle n-oxide (4); Bulletin De La Societe Chimique De France; 1970; pp. 1157-1167 (also as XP009516933); No. 3; France.

\* cited by examiner

2(1H)-PYRIDINONES AND THEIR USE TO TREAT INFLAMMATORY CONDITIONS

CROSS REFERENCE TO RELATED APPLICATIONS

The present application is a U.S. National Phase Application under 35 U.S.C. § 371 of International Application No. PCT/EP2020/062130, filed on Apr. 30, 2020, which claims priority to International Application No. PCT/CN2019/086910, filed on May 14, 2019, and European patent application No. 19180529.0 filed on Jun. 17, 2019, the contents of which are incorporated herein in their entireties.

FIELD OF THE INVENTION

The present invention relates to a novel compound and to a process to prepare it. It further relates to a cosmetic composition that prevents or reduces inflammation. The composition could be delivered in the form of a scalp, hair, skin, or oral care product.

BACKGROUND OF THE INVENTION

Inflammation, a complicated biological host response to harmful stimuli, is a mechanism by which the host removes the stimuli and initiates the healing process for self-protection. The innate immune system for a host is the first line of defence against invading organisms in a non-specific manner. Dysregulated inflammation may cause various personal care problems including dandruff (on scalp/hair), eczema/acnes (on skin), and gingivitis/periodontitis (in the oral cavity). To assist the host organism (e.g. the human or animal) several anti-inflammatory agents either through topical application or through oral consumption have been developed and used to mitigate the above problems.

Dandruff is a condition experienced by many people worldwide. The dandruff condition varies from mild symptoms such as flaking skin to severe inflammation and itchiness of the scalp. *Malassezia* yeasts, such as *Malassezia furfur*, are believed by some to be the main cause of dandruff and, whilst this might not represent the full scientific picture of the situation, *Malassezia* yeasts do appear to be closely associated with dandruff. Hence, the strategy conventionally used for the treatment of dandruff is the topical application of antifungals such as zinc pyrithione (ZnPTO), piroctone olamine, climbazole and ketoconazole which are normally delivered through a shampoo. Additionally, anti-inflammatory agents have also been used in anti-dandruff products to alleviate the ill-effects of this condition.

On the skin, one of the problems experienced by many people, especially on the face, is acne. This has a displeasing cosmetic appearance. Acne, also known as Acne vulgaris, is a common skin condition that affects nearly all adolescents and adults at some time in their lives. It has a complex etiology, involving abnormal keratinization, excess sebum production, androgen function, bacterial growth, and immune hypersensitivity. Although one or more of the above processes is correlated with acne, the one triggering factor and the exact sequence of events leading to the formation of acne lesions has not been fully understood. Other factors which have been linked to acne are presence of free radicals with subsequent oxidative stress leading to cellular damage. It has been observed that acne usually occurs in areas rich in sebaceous glands like the face, neck and back. A bacteria *Propionibacterium acnes* (*P. acnes*) has also been implicated in occurrence of acne.

Acne has been treated in many ways. Most treatments take several weeks to months before a noticeable change is seen. Benzoyl peroxide which has an antibacterial effect has been used for mild cases of acne and is also believed to prevent formation of further acne. In very severe cases of acne, antibiotics like tetracycline, erythromycin and clindamycin have been used. Antibiotics are believed to work by several mechanisms, the most important being the decrease in the number of bacteria in and around the follicle. They are also thought to reduce the irritating chemicals produced by the white blood cells in the sebum, thereby reducing the inflammatory response.

Gingivitis is an inflammatory process of the gums caused by accumulation of plaque and/or bacteria. During gingivitis, the bacteria residing in the dental plaque biofilms and its corresponding components interact with gingival tissues. Following this, innate immune response is activated, characterised by the release of pro-inflammatory cytokines. Gingivitis is a mild phase of periodontal disease and defined as reversible inflammation. It is believed that good habit of oral hygiene e.g. brushing and using mouthrinse product with therapeutic anti-microbial and anti-inflammatory efficacy can be an effective way for individuals to reduce the plaque build-up that causes gingivitis.

Chronic gingivitis results in mild bleeding from the gums during tooth brushing. Gingivitis can progress to a more severe state (chronic periodontitis) when the inflammatory process extends to the periodontal ligament and alveolar bone and/or exert a significant systemic impact on health. Chronic periodontitis is asymptomatic until teeth shift, loosen, or are lost.

Thus, inflammation is a process that is manifest on the topical surface of the human or animal body in one or all of the above described conditions. People have attempted to alleviate the symptoms of the above conditions by developing new actives as well as exploring combination of actives that exhibit synergistic anti-inflammatory benefits.

Piroctone olamine (also known as Octopirox®) is a compound often used in the treatment of fungal infections. Piroctone olamine is the ethanolamine salt of the hydroxamic acid derivative piroctone. It is often used in anti-dandruff shampoo as a replacement for the commonly used compound zinc pyrithione. It is well known that piroctone olamine is light instable, which causes the color of products turning to yellow when exposed to light.

DE 102007045241A1 (Beiersdorf AG) discloses cosmetic or dermatological preparation comprising one or more piroctone olamines and one or more stabilizing agents selected from the group of benzaldehydes and/or alkanediols and/or triols.

Introduction of piroctone olamine from Spec-Chem Ind. discloses hair care compositions comprising piroctone olamine and the antidandruff and antimicrobial efficacy of piroctone olamine.

Introduction of antidandruff active ingredient Octopirox® from Clariant discloses that the Octopirox® is unstable under light. It also discloses the compositions comprising Octopirox® and the production of Octopirox®.

SUMMARY OF THE INVENTION

The present inventors have surprisingly found a new compound which is one of the degradation products of piroctone olamine and it can function as anti-inflammatory active.

In accordance with a first aspect, disclosed is compound of formula 1

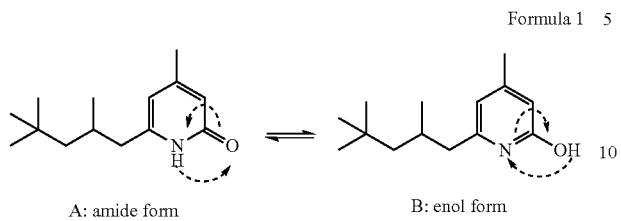

A: amide form    B: enol form

Formula 1

In accordance with a second aspect, disclosed is a process of preparing a compound of the first aspect comprising the steps of:
 i) preparing a solution of piroctone olamine by dissolving piroctone olamine in organic solvents or aqueous surfactant solutions;
 ii) exposing said solution to UV light of 100 mW to 2000 mW in a UV chamber for 0.5 hour to 8 hours to cause degradation of piroctone olamine to form degradation products of said piroctone olamine;
 iii) separating said degradation products of piroctone olamine to a chromatographic technique to get said compound of the formula 1.

In accordance with another aspect, disclosed is a cosmetic composition comprising a compound of the first aspect and a cosmetically acceptable base.

In accordance with another aspect of the present invention, disclosed is a method of treating an inflammatory condition of the skin, or scalp or oral cavity of human or an animal comprising a step of applying thereon a compound of the first aspect.

DETAILED DESCRIPTION OF THE INVENTION

For the avoidance of doubt, any feature of one aspect of the present invention may be utilized in any other aspect of the invention. The word "comprising" is intended to mean "including" but not necessarily "consisting of or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated. As used herein, the indefinite article "a" or "an" and its corresponding definite article "the" means at least one, or one or more, unless specified otherwise. The various features of the present invention referred to in individual sections above apply, as appropriate, to other sections mutatis mutandis. Consequently, features specified in one section may be combined with features specified in other sections as appropriate. Any section headings are added for convenience only, and are not intended to limit the disclosure in any way.

By "a cosmetic composition" as used herein, is meant to include a composition for topical application to the skin of mammals, especially human beings. Such a composition may be generally classified as leave-on or rinse off but is preferably of the leave on type. The composition is formulated into a product which is applied to a human body specifically for improving appearance but may, in addition, also provide cleansing, odor control or general aesthetics. The composition of the present invention can be in the form of a liquid, lotion, cream, foam, scrub, gel, or toner, or applied with an implement or via a face mask or a pad. Non-limiting examples of such compositions include leave-on skin lotions, creams, antiperspirants, deodorants, lipsticks, foundations, mascara, sunless tanners and sunscreen lotions. The composition of the present invention is preferably a leave-on composition. "Skin" as used herein is meant to include skin on the face and body (e.g., neck, chest, back, arms, underarms, hands, legs, buttocks and scalp) and especially to the sun exposed parts thereof.

By "hair care composition" as used herein, is meant to include a composition for topical application to hair or scalp of mammals, especially humans. By topical is meant that the composition is applied to the external surface of the body. In the present invention this is achieved by applying the composition on the hair or scalp. Such a composition may be generally classified as leave-on or rinse off, and includes any product applied for improving the appearance, cleansing, odor control or general aesthetics of scalp and hair. The hair care composition of the present invention could be in the form of a liquid, lotion, cream, foam, scrub, gel, shampoo, conditioner, shower gel or bar. The haircare composition of the present invention is preferably a leave-on composition. Alternatively, the hair care composition of the present invention is a wash-off composition. Compositions for achieving the desired benefits by way of ingestion into the human body are excluded from the scope of the present invention.

The New Compound

The compound in accordance with this invention is a compound of the formula 1, which may exist in amide form A or enol form B:

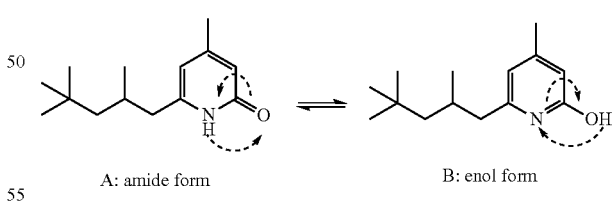

A: amide form    B: enol form

Formula 1

It is especially preferred that the compound of the formula 1 is the one with the enol form.

The pH of the composition can impact the structure of the compound of the formula 1. The amide form dominates when the pH is below 7, and it is enol form dominates when the pH is greater than 7.

The compound of the formula 1 of the present invention can be prepared by a process comprising the steps of:
 i) preparing a solution of piroctone olamine by dissolving piroctone olamine in an organic solvent or in water comprising at least one surfactant;

ii) exposing said solution to UV light of 100 mW to 2000 mW in a UV chamber for 0.5 hour to 8 hours to cause degradation of piroctone olamine to form degradation products of said piroctone olamine;
iii) separating said degradation products of piroctone olamine to a chromatographic technique to get said compound of the formula 1.

In step ii), the time of exposing said solution under UV radiation depends on the intensity of UV radiation. The intensity of UV radiation has to be at least 100 mW. When it's exposed under UV light of 100 mW, it needs about 8 hours.

It is preferred that the organic solvent of step (i) is an alcohol. It is more preferred that the organic solvent of step (i) is methanol or ethanol.

It is preferred that the aqueous surfactant solutions of step (i) comprise an anionic surfactant or a non-ionic surfactant.

It is preferred that the chromatographic technique used in step iii) is selected from Preparation Liquid Chromatography (pre-LC) with a Preparative LC column, or column chromatography, or Thin Layer Chromatography (TLC).

It is particularly preferred that the chromatographic technique used in step iii) is preparation liquid chromatography (pre-LC) with a preparative LC column (Shiseido, 20*250 mm, 5 μm). A preferred method is described below:

The column is eluted with methanol and water at a flow rate of 15 mL/minute (5 mL/minute for second purification). The eluent is consecutively collected into a series of sample tubes (15 mL/tube). After separated by preparative chromatography, the eluent solution in each sample tube is analyzed using a HPLC-UV. The eluent solution tubes which were confirmed to contain the compound of formula 1 are collected and dried to get the compound of formula 1 in powder form.

Once this compound is prepared, it is generally included at 0.01 to 10 wt %, preferably at 0.1 to 5 wt %, more preferably at 0.5 to 2.5 wt % by weight of the cosmetic composition.

The composition of the invention comprises a cosmetically acceptable carrier. The composition of the invention may be prepared so that it is suitable for use as a scalp, hair care, skin, or an oral care product. The product may be delivered in the form of a solid, soft solid, liquid, emulsion, microemulsion, lotion, cream, gel, or aerosol forms.

Hair Care Composition

In accordance with a further aspect of the invention is disclosed a hair care composition comprising composite particles of the first aspect. Preferably the composition is a shampoo, hair conditioner, hair cream, hair gel, hair serum, mousse or a hair oil. More preferably the composition is a shampoo composition.

The composition of the invention especially shampoos are formulated with an anionic surfactant e.g. an alkyl sulphate and/or ethoxylated alkyl sulfate surfactant. These anionic surfactants are preferably present at a level of from 1 to 20%, preferably 2 to 16%, furthermore preferably from 3 to 16% by weight of the composition. Preferred alkyl sulfates are C8-18 alky sulfates, more preferably C12-18 alkyl sulfates, preferably in the form of a salt with a solubilising cation such as sodium, potassium, ammonium or substituted ammonium.

Preferred alkyl ether sulfates are those having the formula: $RO(CH_2CH_2O)_nSO_3M$; wherein R is an alkyl or alkenyl having from 8 to 18 (preferably 12 to 18) carbon atoms; n is a number having an average value of greater than at least 0.5, preferably between 1 and 3, more preferably between 2 and 3; and M is a solubilising cation such as sodium, potassium, ammonium or substituted ammonium. An example is sodium lauryl ether sulfate (SLES). Preferred ethoxylated alkyl sulfate anionic surfactant is sodium lauryl ether sulfate (SLES). SLES having an average degree of ethoxylation of from 0.5 to 3, preferably 1 to 3 is especially preferred.

Shampoo compositions according to the invention may comprise one or more further anionic cleansing surfactants which are cosmetically acceptable and suitable for topical application to the hair.

A composition of the invention preferably additionally comprises an amphoteric surfactant preferably a betaine surfactant preferably an alkyl amidopropyl betaine surfactant for example cocamidopropyl betaine. In a preferred embodiment, the composition comprises from 0.1 to 10 wt. %, preferably from 0.5 to 8 wt. %, more preferably from 1 to 5 wt. % of a betaine surfactant.

To enhance deposition of actives from compositions of the invention especially shampoos, cationic polymers are generally included therein. In the present invention too, it is preferred that the composition additionally includes 0.01 to 2.0% of a cationic polymer. The cationic polymer is preferably guar hydroxypropyl trimonium chloride. Guar polymer predominantly contains galactomannan polymer chains. This polymer is available at various molecular weights and degree of cationic substitutions depending on how much the guar has been hydrolysed and cationised. The cationic polymer is preferably present in 0.04 to 0.5%, more preferably 0.08 to 0.25% by weight of the composition.

When conditioning benefits are to be delivered through the composition of the invention the composition is called a hair conditioner. Typically, the most popular conditioning agents used in hair care compositions are water-insoluble oily materials such as mineral oils, naturally occurring oils such as triglycerides and silicone polymers. Conditioning benefit is achieved by the oily material being deposited onto the hair resulting in the formation of a film, which makes the hair easier to comb when wet and more manageable when dry. An especially useful conditioning agent is a silicone compound, preferably a non-volatile silicone compound. Advantageously compositions herein may include one or more silicones. The silicones are conditioning agents found in dispersed or suspended particulate form. They are intended to deposit onto hair remaining behind after rinsing of the hair with water. Suitable silicone oils may include polyalkyl siloxanes, polyaryl siloxanes, polyalkylaryl siloxanes, polyether siloxane copolymers and mixtures thereof. Amino silicones are often formulated with shampoo compositions. Amino silicones are silicones containing at least one primary amine, secondary amine, tertiary amine or a quaternary ammonium group. High molecular weight silicone gums can also be utilized. Another useful type are the crosslinked silicone elastomers such as Dimethicone/Vinyl/Dimethicone Crosspolymers (e.g. Dow Corning 9040 and 9041).

Amounts of the silicone in compositions where present may range from about 0.1 to about 10 wt. %, preferably from about 0.1 to about 8 wt. %, more preferably from about 0.3 to about 5 wt. % by weight of the hair care compositions.

The pH of the composition is preferably equal to or higher than 4.0, more preferably in the range of 5.0 to 7.0.

The hair conditioning composition usually comprises conditioning surfactants selected from cationic surfactants, used singly or in admixture. Suitable cationic surfactants for use in conditioner compositions according to the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride (eg, Arquad 2HT/75 from Akzo Nobel), cocotrimethylammonium chloride, PEG-2-oleammonium chloride and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in conditioners according to the invention is cetyltrimethylammonium chloride, available commercially, for example as GENAMIN CTAC, ex Hoechst Celanese. Another particularly useful cationic surfactant for use in conditioners according to the invention is behenyltrimethylammonium chloride, available commercially, for example as GENAMIN KDMP, ex Clariant. Yet another preferred cationic surfactant is stearamidopropyl dimethylamine.

The most preferred cationic surfactants for use in the composition are stearamidopropyl dimethylamine, behentrimonium chloride, or stearyl trimethyl ammonium chloride. In conditioners of the invention, the level of cationic surfactant will generally range from 0.1% to 5%, preferably 0.5 to 2.5% by weight of the composition.

Hair conditioning compositions of the invention preferably may also additionally comprise a fatty alcohol. The combined use of fatty alcohols and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 22. Fatty alcohols are typically compounds containing straight chain alkyl groups. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol in conditioners of the invention will generally range from 0.5 to 10%, preferably from 0.1% to 8%, more preferably from 0.2% to 7%, most preferably from 0.3% to 6% by weight of the composition. The weight ratio of cationic surfactant to fatty alcohol is suitably from 1:1 to 1:10, more preferably from 1:1.5 to 1:8, optimally from 1:2 to 1:5.

Hair care compositions whether delivered as shampoos or conditioners usually comprise an anti-dandruff agent. The most preferred anti-dandruff agent for use in the compositon of the invention is a zinc based anti-dandruff agent preferably zinc pyrthione. Zinc pyrithione belongs to the class of insoluble metal pyrithione which may be represented by the following general formula:

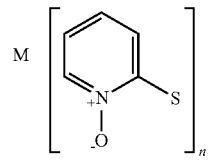

in which M is a polyvalent metal ion and n corresponds to the valency of M. In the present invention M corresponds to Zinc and n has the value of 2.

The zinc pyrithione may have any particle form suitable for use in a composition for topical application. For example, the zinc pyrithione may be in the form of amorphous or crystalline particles having a range of different particle sizes. The zinc pyrithione may, for example, be in the form of particles having a size distribution in which at least about 90% of the particles have a size of up to 100 microns, more preferably up to 50 microns, even more preferably up to 10 microns, most preferably 5 microns or less.

Various methods for producing fine particles of metal pyrithione are described, for example, in EP-A-0 173 259. Suitable methods for determining particle size are described in that document. The insoluble metal pyrithione may be made up of one particulate form or two or more different particulate forms.

Other suitable particulate forms for the zinc pyrithione include platelets and needle-shaped particles. Platelets of zinc pyrithione are described in EP-A-0034385, the contents of which are incorporated herein by reference. The needle shaped particles are preferably of the type described in WO99/66886, the contents of which are incorporated herein by reference. For needle-shaped particles preferably at least 50% by number of the particles are needle-shaped particles having a length of between 1 μm and 50 μm.

The amount of metal pyrithione incorporated into the compositions may depend on the type of composition and the exact nature of the material used. A preferred amount of pyrithione is from about 0.01% to about 1.5% by weight of the total composition, more preferably from about 0.05% to about 1.5% by weight of the total composition.

The composition as per the invention especially for antidandruff shampoos preferably additionally comprises a zinc compound. The presence of additional zinc compound in the composition is believed to improve the antidandruff efficacy of the zinc based antidandruff agent. Suitable zinc compounds are zinc oxide, zinc citrate, zinc malonate, zinc carbonate or combinations thereof. The zinc compound is preferably present in 0.1 to 3%, more preferably 0.1 to 1.5% by weight of the composition.

The composition as per the invention may also comprises an antidandruff agent selected from azoles, Octopirox® (piroctone olamine), selenium sulfide, salicylic acid and combinations thereof. Azoles include ketoconazole and climbazole, preferably climbazole.

The azole fungicide is preferably included in 0.01 to 2%, more preferably 0.025 to 0.75% by weight of the composition. The presence of a conazole fungicide is believed to improve the deposition of zinc pyrithione.

It is further preferred that the hair care composition of the invention comprises a cosmetic ingredient. Preferably the cosmetic ingredient is selected from the group consisting of a silicone, an antibacterial agent other than antidandruff agents, a foam booster, a perfume, encapsulates (for example encapsulated fragrance) a dye, a colouring agent, a pigment, a preservative, a thickener, a protein, a phosphate ester, a buffering agent, a pH adjusting agent, a pearlescer (for example; mica, titanium dioxide, titanium dioxide coated mica, ethylene glycol distearate (INCI glycol distearate)) and/or opacifier, a viscosity modifier, an emollient, a sunscreen, an emulsifier, a sensate active (for example menthol and menthol derivatives), vitamins, mineral oils, essential oils, lipids, natural actives, glycerin, natural hair nutrients such as botanical extracts, fruit extracts, sugar derivatives and amino acids, microcrystalline cellulose and mixtures thereof.

Preferably, the hair care composition of the present invention includes from 0.01 to 20 wt % of the at least one cosmetic ingredient, more preferably from 0.05 to 10 wt %, still more preferably from 0.075 to 7.5 wt % and most preferably, from 0.1 to 5 wt % of the at least one cosmetic ingredient, by weight of the total composition.

The hair care composition of the present invention may also comprise synergistic antimicrobial compounds that give synergistic antimicrobial benefit when used in combination with the antidandruff active (for example zinc pyrithione) to enhance its properties and further inhibit the growth of *Malassezia furfur*. Non-limiting examples of these compounds include compounds having alcoholic groups (e.g. honokiol, magnolol or paeonol), Piperazines and a phenolic compound found in natural plant extract viz. thymol and terpeniol.

The composition may additionally comprise a vitamin B3 compound. The preferred vitamin B3 compound is niacinamide.

Niacinamide is known for secretion of AM Ps (Anti-Microbial Proteins) from keratinocytes. The AM Ps thus secreted provides for improving immunity of e.g. the scalp. Thus, with the use of niacinamide, the anti-dandruff efficacy can be enhanced not just through anti-fungal activity but by boosting the scalp's own protection shield against germs, through use of niacinamide. This combination could provide further long-lasting protection e.g. up to 24 hours of protection against germs.

When present, it is preferred that the hair care composition of the invention comprises 0.1 to 5% niacinamide, more preferably 0.5 to 5%, furthermore preferably 0.5 to 3%, and optimally 1.0 to 3.0% by weight of the composition.

Skin Care

The composition of the invention may be used for skin care. The cosmetically acceptable base in such cases may be a liquid or solid material. Typically, base is present in an amount ranging from 10 to 99.9%, more preferably from 20 to 95%, most preferably from 40 to 85% by total weight of the composition including all ranges subsumed therein. It is particularly preferred that the cosmetically acceptable carrier includes water. Water is preferably included in an amount from 30 to 90%, more preferably from 30 to 85%, most preferably from 30 to 80% by total weight of the sunscreen composition. Besides water, suitable carrier classes include silicones, polyhydric alcohols, hydrocarbons, triglycerides and thickening powders.

The skin care composition of the invention may be in any form including toners, lotions, creams, mousses, scrub, serum or gel that is suitable for topical application to the skin. The composition can be either a leave-on product such as skin lotions, creams, antiperspirants, deodorants, lipsticks, foundations, mascara, sunless tanners and sunscreen lotions or a rinse-off product such as shower gels and toilet bars. It is preferred that the composition is a skin lotion or a cream.

The composition may comprise an emollient oil that act as a co-solvent. Suitable emollient oils include, for example, ester of alkoxylated aromatic alcohol with fatty carboxylic acid, esters of polyglycols or diols with fatty carboxylic acid such as caprylic/capric triglyceride, ester of fatty alcohol and fatty acid, alkoxylated derivative of benzyl alcohol and mixtures thereof. Preferably the emollient oil is caprylic/capric triglyceride.

Typically, such compositions comprise co-solvent in an amount from 0.01 to 10%, more preferably from 0.1 to 8%, most preferably from 1 to 6%, based on the total weight of the sunscreen composition and including all ranges subsumed therein.

The composition may additionally comprise sunscreen agents such as inorganic sunscreens. For example, zinc oxide, titanium dioxide, iron oxide, silica such as fumed silica. The amount of such sunscreen agents is preferably incorporated from 0.1 to 5% by total weight of the sunscreen composition.

The composition of the invention may comprise a UV-A sunscreen agent selected from the group consisting of a dibenzoylmethane derivative, a triazine derivative, a benzophenone derivative and mixtures thereof. In a preferred embodiment, the UV-A sunscreen agent comprises or is a dibenzoylmethane derivative, for example, butyl methoxydibenzoylmethane (sold under the trade name Parsol 1789).

Typically, the sunscreen composition of the present invention comprises from 0.1 to 15% by weight of the UV-A sunscreen agent, more preferably from 0.1 to 10%, most preferably from 1 to 5%, based on the total weight of the composition and including all ranges subsumed therein.

The composition of the invention may also comprise a UV-B sunscreen agent. Suitable UV-B sunscreen agent of the invention is selected from the group consisting of a benzophenone, an anthranilate, a salicylate, a cinnamate, a camphor, benzylidene malonate, a triazone, and derivatives thereof. In a preferred embodiment, the UV-B sunscreen agent comprises or is a cinnamate derivative, for example, ethylhexyl methoxycinnamate (sold under the trade name Parsol MCX).

Typically, the composition comprises from 0.1 to 20% by weight of the UV-B sunscreen agent, more preferably from 0.5 to 18%, most preferably from 1 to 15%, based on the total weight of the composition and including all ranges subsumed therein.

A skin lightening agent may also be incorporated into the composition of the invention.

Most preferred skin lightening active is a Vitamin B3 compound. Vitamin B3 compound maybe nicacin, nicotinic acid or niacinamide, preferably niacinamide. Niacinamide has the structure given below:

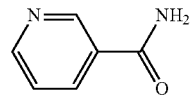

Niacinamide is preferably present in 0.01 to 5%, more preferably 0.1 to 3% by weight of the composition. Suitable skin lightening agents other than Vitamin B3 and its derivatives are kojic acid, arbutin, tranexamic acid, placental extract, ascorbic acid and its derivatives (e.g. magnesium ascorbyl phosphate, sodium ascorbyl phosphate, ascorbyl glucoside, and ascorbyl tetraisopalmitates), aloe extract, ammonium lactate, azelaic acid, citrate esters, ellagic acid, glycolic acid, green tea extract, hydroquinone, lemon extract, linoleic acid, vitamins like vitamin B6, vitamin B12, vitamin C, vitamin A, a dicarboxylic acid, resorcinol derivatives, hydroxycarboxylic acid like lactic acid and their salts (e.g. sodium lactate) or a mixture thereof. Typically, the skin lightening agent is present in an amount from 0.1 to 10%, more preferably from 0.2 to 5%, most preferably from 0.3 to 3% by total weight of the composition including all ranges subsumed therein.

A specific class of skin care compositions is what is known as deodorant compositions. These can be applied cosmetically and topically to the skin, broadly speaking, by one of two methods. Different consumers prefer one method or the other. In one method, sometimes called a contact method, a composition is wiped across the surface of the skin, depositing a fraction of the composition as it passes. In the second method, sometimes called the non-contact method, the composition is sprayed from a dispenser held proximate to the skin, often in the region of 10 to 20 cm. The spray can be developed by mechanical means of generating pressure on the contents of the dispenser, such as a pump or a squeezable sidewall or by internally generated pressure arising from a fraction of a liquefied propellant volatilising, the dispenser commonly being called an aerosol.

There are broadly speaking two classes of contact compositions, one of which is liquid and usually applied using a roll-on dispenser or possibly absorbed into or onto a wipe, and in the second of which the desired active is distributed within a carrier liquid that forms a continuous phase that has been gelled. In one variation, the carrier fluid comprises a solvent for the desired active and in a second variation, the active remains as a particulate solid that is suspended in an oil, usually a blend of oils.

Stick or Soft Solid Compositions

Many different materials have been proposed as gellant for a continuous oil phase, including waxes, small molecule gelling agents and polymers. They each have their advantages and of them, one of the most popular class of gellant has comprised waxes, partly at least due to their ready availability and ease of processing, including in particular linear fatty alcohol wax gellants. A gelled deodourant composition is applied topically to skin by wiping it across and in contact with the skin, thereby depositing on the skin a thin film.

The nature of the film depends to a significant extent on the gellant that is employed. Although wax fatty alcohols have been employed as gellant for many years, and are effective for the purpose of gelling, the resultant product is rather ineffective at improving the visual appearance of skin, and in particular underarm skin, to which the composition has been applied. This problem has been solved by including ameliorating materials for example, di or polyhydric humectants and/or a triglyceride oil.

Roll-On

Liquid compositions that are applicable from a roll-on broadly speaking can be divided into two classes, namely those in which an active is suspended in a hydrophobic carrier, such as a volatile silicone and those in which the active is dissolved in a carrier liquid. The latter has proven to be more popular. There are mainly two sorts of dissolving carrier liquid, namely carriers that are predominantly alcoholic, which is to say the greater part of the dissolving carrier fluid comprises ethanol and the second class in which the carrier liquid is mainly water. The former was very popular because ethanol is a mild bactericide in its own right, but its popularity waned because it stings, especially if the surface onto which the composition has been applied has been damaged or cut, such as can easily arise during shaving or other de-hairing operations.

The second class of formulations that is an alternative to alcoholic formulations comprise a dispersion of water-insoluble or very poorly water-soluble ingredients in an aqueous solution of the active. Herein, such compositions will be called emulsions.

Roll-on emulsions commonly comprise one or more emulsifiers to maintain a distribution of the water-soluble ingredients.

Aerosol Compositions

Deodorant compositions may be delivered through an aerosol which comprises a propellant in addition to the other ingredients described hereinabove. Commonly, the propellant is employed in a weight ratio to the base formulation of from 95:5 to 5:95. Depending on the propellant, in such aerosol compositions the ratio of propellant to base formulation is normally at least 20:80, generally at least 30:70, particularly at least 40:60, and in many formulations, the weight ratio is from 90:10 to 50:50. A ratio range of from 70:30 to 90:10 is sometimes preferred.

Propellants herein generally accord with one of three classes; i) low boiling point gasses liquefied by compression, ii) volatile ethers and iii) compressed non-oxidising gases.

Class i) is conveniently a low boiling point material, typically boiling below −5° C., and often below −15° C., and in particular, alkanes and/or halogenated hydrocarbons. This class of propellant is usually liquefied at the pressure in the aerosol canister and evaporates to generate the pressure to expel the composition out of the canister. Examples of suitable alkanes include particularly propane, butane or isobutene. The second class of propellant comprises a very volatile ether of which the most widely employed ether hitherto is dimethyl ether. This propellant can advantageously be employed at relatively low weight ratio of propellant to base formulation, for example to as low as 5:95. It can also be employed in admixture with, for example, compressible/liquefiable alkane gasses. The third class of propellant comprises compressed non-oxidising gasses, and in particular carbon dioxide or nitrogen. Inert gases like neon are a theoretical alternative.

Skin care compositions may also comprise other ingredients which are common in the art to enhance physical properties and performance. Suitable ingredients include but are not limited to humectants, thickeners, opacifiers, binders, colorants and pigments, pH adjusting agents, preservatives, optics, perfumes, viscosity modifiers, biological additives, buffering agents, conditioners, natural extracts, essential oils and skin benefit agents including anti-inflammatory agents, cooling agents, antiperspirant agents, anti-aging agents, anti-acne agents, anti-microbial agents and antioxidants.

Oral Care

When the personal care composition is delivered for oral care, it includes a cosmetically acceptable base which may be an abrasive, a thickener, a humectant or an orally acceptable surfactant. The product may be delivered in the form of an ointment, a gel, a dentifrice or a mouthwash.

Oral care compositions preferably comprise an abrasive. Gels usually contain silica, whereas opaque creams generally contain calcium-based abrasives, especially chalk.

Preferred toothpaste compositions have 5 to 60 wt % calcium-based abrasive. In more preferred compositions it is 30 to 60 wt % and furthermore preferably from 35 to 55 wt %. Optimal compositions have 40 to 55 wt % calcium-based abrasive.

A preferred abrasive is fine ground natural chalk (FGNC), which is a form of chalk. It is obtained from limestone or marble. FGNC may also be modified chemically or physically by coating during milling or after milling by heat treatment. Typical coating materials include magnesium stearate or oleate. The morphology of FGNC may also be modified during the milling process by using different milling techniques, for example, ball milling, air-classifier milling or spiral jet milling.

FGNC may be used as the sole calcium-based abrasive. However, FGNC may also be used with the other calcium-based abrasives for some balance of abrasion. Usually the particle size of chalk is from 1 to 60 μm, and preferred sizes range from 1 to 15 μm. Other preferred calcium-based abrasives include dicalcium phosphate (DCP), calcium pyrophosphate and precipitated calcium carbonate (PCC), which preferably are included at 25 to 55 wt %, more preferably 35 to 50 wt %.

When a combination of calcium-based abrasives is desired, it is preferred that FGNC is 35 to 100%, more preferably 75 to 100% and especially from 95 to 100% of the total amount of Calcium based abrasives. In such cases, the balance, most preferably, is PCC.

Other abrasives may also be used depending upon the intended degree of abrasion. These include synthetic abrasive polishing agents such as amorphous precipitated silica and silica gels. Other abrasive agents include magnesium carbonate, sodium metaphosphate, potassium metaphosphate, zirconium silicate, potassium metaphosphate, magnesium orthophosphate, tricalcium phosphate, magnesium orthophosphate, trimagnesium phosphate, aluminum silicate, zirconium silicate and perlite.

In a preferred embodiment, the composition comprises a thickener. Thickeners that may be used in this invention include, sodium carboxymethyl cellulose (SCMC), hydroxyl ethyl cellulose, methyl cellulose, ethyl cellulose, gum tragacanth, gum arabic, gum karaya, xanthan gum, sodium alginate, carrageenan gum, guar gum, Irish moss, starch, modified starch, silica based thickeners including silica aerogels, magnesium aluminum silicate (e.g., Veegum®), Carbomers (cross-linked acrylates) and mixtures thereof.

Typically, thickening silica, sodium carboxymethyl cellulose and/or a Carbomer is/are preferred thickeners for use in the composition of the invention. When a Carbomer is employed, those having a weight-average molecular weight of at least 700,000 are desired, and preferably, those having a molecular weight of at least 1,200,000, and most preferably, those having a molecular weight of at least about 2,500,000 are desired. Mixtures of Carbomers may also be used herein.

In an especially preferred embodiment, the Carbomer is Synthalen® PNC, Synthalen® KP or a mixture thereof. It has been described as a high molecular weight and cross-linked polyacrylic acid and identified via CAS number 9063-87-0. These types of materials are available commercially from suppliers like Sigma.

In another especially preferred embodiment, the sodium carboxymethyl cellulose (SCMC) used is SCMC 9H. It has been described as a sodium salt of a cellulose derivative with carboxymethyl groups bound to hydroxy groups of glucopyranose backbone monomers and identified via CAS number 9004-32-4. The same is available from suppliers like Alfa Chem.

Thickening silica is especially preferred to be used in gel toothpastes. Gel toothpastes generally contain up to 8.5 wt % thickening silica whereas opaque toothpastes typically contain 3 to 4 wt % thickening silica.

When present, preferred thickening silicas include AEROSIL T series from Degussa or the CAB-O-SIL series from Cabot Corporation, silica gels such as the SYLODENT or SYLOX series from W. R. Grace & Co or precipitated silica such as ZEOTHIX 265 from J. M. Huber Corporation. Useful silica thickeners also include ZEODENT 165, ZEODENT 163 and/or 167 and ZEOFREE 153, 177, and/or 265 silicas, all available from J. M. Huber Corporation. Other preferred thickening silicas include MFIL, MFIL-P (From Madhu Silica, India), SIDENT 22 S and AEROSIL 200 (Ex. Evonik Industries), SYLODENT and PERKASIL thickening silicas from WR Grace & Company and Tixosil 43 and 331 from Rhodia, synthetic finely divided pyrogenic silica such as those sold under the trademarks SYLOID 244, SYLOID 266 and AEROSIL D-200.

Thickener, when present, preferably makes up from 0.01 to about 10%, more preferably from 0.1 to 9%, and most preferably, from 1.5 to 8% by weight of the composition.

Suitable humectants are preferably used in the oral care composition of the present invention and they include, for example, glycerin, sorbitol, propylene glycol, dipropylene glycol, diglycerol, triacetin, mineral oil, polyethylene glycol (preferably, PEG-400), alkane diols like butane diol and hexanediol, ethanol, pentylene glycol, or a mixture thereof. Glycerin, polyethylene glycol, sorbitol or mixtures thereof are the preferred humectants.

The humectant may be present in the range of from 10 to 90% by weight of oral care compositions. More preferably, the humectant makes up from 25 to 80%, and most preferably, from 45 to 70% by weight of the composition, based on total weight of the composition and including all ranges subsumed therein.

Preferably, an oral care composition comprises a surfactant. Preferably the composition comprises at least 0.01% surfactant by weight of the composition, more preferably at least 0.1% and most preferably from 0.5 to 7%. Suitable surfactants include anionic surfactants, such as the sodium, magnesium, ammonium or ethanolamine salts of C8 to C18 alkyl sulphates (for example sodium lauryl sulphate), C8 to C18 alkyl sulphosuccinates (for example dioctyl sodium sulphosuccinate), C8 to C18 alkyl sulphoacetates (such as sodium lauryl sulphoacetate), C8 to C18 alkyl sarcosinates (such as sodium lauryl sarcosinate), C8 to C18 alkyl phosphates (which can optionally comprise up to 10 ethylene oxide and/or propylene oxide units) and sulphated monoglycerides. More preferably the surfactant comprises or is an anionic surfactant. The preferred anionic surfactants are sodium lauryl sulphate and/or sodium dodecylbenzene sulfonate. Most preferably the surfactant is sodium lauryl sulphate. Other suitable surfactants include nonionic surfactants, such as optionally polyethoxylated fatty acid sorbitan esters, ethoxylated fatty acids, esters of polyethylene glycol, ethoxylates of fatty acid monoglycerides and diglycerides, and ethylene oxide/propylene oxide block polymers. Other suitable surfactants include amphoteric surfactants, such as betaines or sulphobetaines. Mixtures of any of the above described materials may also be used. Most preferred surfactants are an alkali metal alkyl sulphate or a betaine.

Water may preferably be included in 5 to 95%, in particular 10 to 75%, and especially at from 10 to 60%, furthermore preferably 10 to 45% by total weight of the composition.

When the oral care composition of this invention is a toothpaste or gel, the same typically has a viscosity from about 30,000 to 180,000 centipoise, and preferably, from 60,000 to 170,000 centipoise, and most preferably, from 65,000 to 165,000 centipoise.

The oral care composition of the present invention may contain a variety of other ingredients which are common in the art to enhance physical properties and performance. These ingredients include antimicrobial, anti-caries agents, plaque buffers, fluoride sources, vitamins, plant extracts, desensitizing agents, anti-calculus agents, biomolecules, flavors, proteinaceous materials, preservatives, opacifying agents, coloring agents, pH-adjusting agents, sweetening agents, particulate abrasive materials, polymeric compounds, buffers and salts to buffer the pH and ionic strength of the compositions, and mixtures thereof. Such ingredients typically and collectively make-up less than 20% by weight of the composition, and preferably, from 0.0 to 15% by weight, and most preferably, from 0.01 to 12% by weight of the composition, including all ranges subsumed therein.

Method and Use

The present invention provides for a non-therapeutic method of reducing inflammation on a topical surface of a human or animal body comprising a step of applying thereon a compound of the first aspect. Preferably it is for cosmetic purpose.

The present invention also provides for a non-therapeutic method of reducing inflammation on a topical surface of a human or animal body comprising a step of applying thereon a composition of the second aspect. Preferably it is for cosmetic purpose.

The method may comprise applying the composition as a leave-on composition. Leave-on compositions are applied on to the desired skin surface and left thereon till the person washes the skin during the normal course of personal washing e.g. when showering or during a bath. Alternately the composition may be a wash-off composition where it is used to clean the body surface and this type of composition includes a soap bar, a body wash or face wash composition or shampoo or hair conditioning composition.

The present invention provides for use of a compound of the first aspect to treat an inflammatory condition of the skin, or scalp or oral cavity of a human or an animal. In one aspect the use is non-therapeutic in nature, preferably cosmetic in nature.

The present invention also provides for use of a composition of the second aspect to treat an inflammatory condition of the skin, or scalp or oral cavity of a human or an animal. In one aspect the use is non-therapeutic in nature, preferably cosmetic in nature.

The invention will be further illustrated by the following, non-limiting Examples, in which all percentages quoted are by weight based on total weight unless otherwise stated.

The examples are intended to illustrate the invention and are not intended to limit the invention to those examples per se.

EXAMPLES

Example 1

Preparation of a Compound of the Formula 1

The compound of the formula 1 used in the experiments was prepared using the following materials, methods and procedures:

UV Treatment:

0.05 g Octopirox® was dissolved in 10 ml methanol in a transparent glass vial. The UV irradiation was carried out in an X-Rite® (Macbeth) Spectra Light III chamber. UV mode was chosen for UV irradiation which provides both UVA and UVB light. The intensity of light in the chamber was fixed (estimated at 250 μw/cm² for UVA and 110 μw/cm² for UVB). The transmittance of UVA and UVB in glass vial was 80.3% and 71.9%, respectively. The chamber temperature was equal to the room temperature (20±2° C.). The sample was placed close to the center of the chamber. After 6 hours, the sample was concentrated by a rotary evaporator.

Separation:

The separation was carried out with a silica gel column (2×48 cm, V=150 mL) filled with 60 g silica gel (200-300 mesh size). The silica gel column was activated and balanced by petroleum ether/ethyl acetate (2/1, v/v). After added to the silica gel column, the concentrated mixture of UV degradation products was separated by the gradient elution with a speed at 6 mL/minute. Then the compound inside the invention was collected by evaporating the solvent with rotary evaporator.

Characterization of Chemical Structure of a Compound of the Formula 1

The Element analysis, IR, MS and NMR analysis were used to confirm the chemical structure of the compound.

Element analysis of the compound was carried out on an Elementar Vario EL III element analyser. Theoretical value of C14H23NO: C, 75.97%; H, 10.47%; N, 6.33%. Measured value: C, 75.84%; H, 10.50%; N, 6.20%.

IR analysis was carried out on a Thermo Nicolet iN10MX-iZ10 FTIR. The compound was tableted with potassium bromide prior to IR analysis. The result is given in Table 1 below:

TABLE 1

| Absorption frequency wavelet (cm$^{-1}$) | Intensity of IR absorptions | Bonds | Groups |
| --- | --- | --- | --- |
| 3279.7 | w | ∪ N—H | 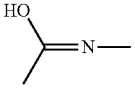 |
| 2951.5 | m | ∪ C—H | —CH$_3$ |
| 2903.9 | m | ∪ C—H | —CH$_2$— |
| 1652.0 | s | ∪ C=O | 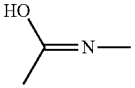 |
| 1624.1 | s | ∪ C=N | >C=N— (pyridine) |
| 1545.7 | m | ∪ C=C | >C=C— (pyridine) |
| 1467.1 | m | δ C—H | —CH$_2$— |
| 1433.7, 1393.1 | m, w | δ C—H | —CH$_3$ |
| 1217.6 | m | ∪ C—O | =C—OH (phenol) |
| 975.3 | m | ∪ C—C | >C=C— (pyridine) |
| 846.9 | m | δ C—H | >C=C—H (pyridine) |

MS analysis was carried out with an Agilent 5973N EI-MS in positive mode. The top 7 MS peaks are listed in below table 2 and the fragments of corresponding MS peaks are shown in the scheme for Fragmentation of the compound in EI-MS.

TABLE 2

| m/z | Relative abundance (%) |
| --- | --- |
| 221 | 6.16 |
| 206 | 11.69 |
| 164 | 10.16 |
| 150 | 7.58 |
| 123 | 100.00 |
| 94 | 7.58 |
| 57 | 11.78 |

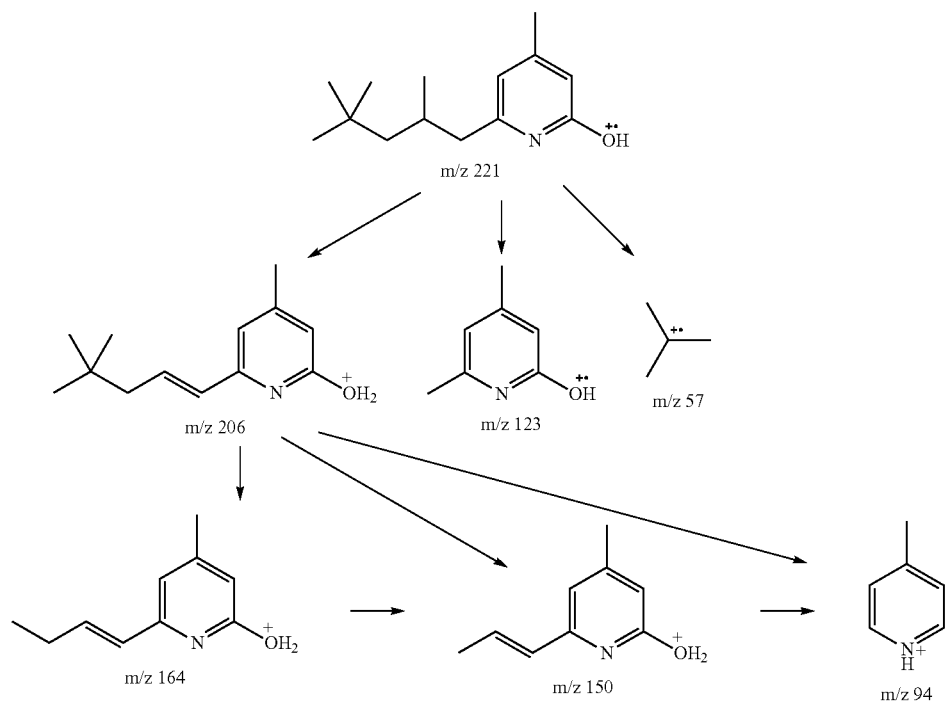

Fragmentation of the compound (taking enol form as example) in EI-MS 1H NMR and 13C NMR analysis were carried out with a Bruker AV-600 NMR. d-Chloroform was used to dissolve the compound. The result (taking enol form as example) is given in Table 3 below:

TABLE 3

| C atom | $^{13}$C NMR (ppm) | $^{1}$H NMR (ppm) | $^{1}$H peak shape | Number of H |
|---|---|---|---|---|
| 2 | 164.68 | | | |
| 3 | 115.21 | 5.97 | s | 1 |
| 4 | 147.79 | | | |
| 5 | 109.69 | 6.25 | s | 1 |
| 6 | 154.04 | | | |
| 1' | 42.81 | 2.30 | dd | 1 |
| | | 2.55 | dd | 1 |
| 2' | 29.57 | 1.94 | m | 1 |
| 3' | 50.47 | 1.14 | m | 1 |
| | | 1.28 | m | 1 |
| 4' | 31.09 | | | |
| 5' | 29.92 | 0.89 | s | 3 |
| 6' | 29.92 | 0.89 | s | 3 |
| 7' | 29.92 | 0.89 | s | 3 |
| 8' | 22.23 | 0.94 | d | 3 |
| 1" | 21.74 | 2.21 | s | 3 |

The above results of Element analysis, IR, MS and NMR analysis confirm that the chemical structure of the compound, which is:

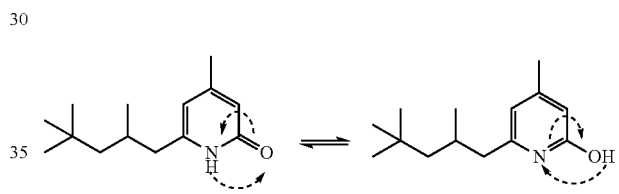

A: amide form   B: enol form

Anti-Inflammation Efficacy of the Compound Inside the Invention in THP-1 Invitro Assay (Using THP-1 Assay)

The following procedure was used to test the anti-inflammation efficacy of the compound:

THP1-XBlue™ (Cat No: thpx-sp, InvivoGen) cells were cultured as suspense in RPMI 1640 medium supplemented with 10% FBS, penicillin (10 U/mL)—streptomycin (10 μg/ML). Cells were differentiated in 24-well plates at the density of $5 \times 10^5$ cells/well with 100 nM PMA for 72 hours. Cells were then co-treated with pure E. coli ipopolysaccharides (LPS) and with the compound inside the invention. After 24 hours, the supernatants were collected and measured for interleukin (IL)-6 as pro-inflammatory bio-marker using enzyme-linked immunosorbent assay (ELISA).

The results in terms of concentration of IL-6 in pg/ml is given in Table 4 below:

TABLE 4

| Examples | Composition | Concentration of IL-6 (pg/ml) | Std. dev |
|---|---|---|---|
| 1 | LPS | 3253.4 | 177.6 |
| 2 | 5 μM of the compound | 3083.3 | 114.3 |
| 3 | 10 μM of the compound | 1405.3 | 214.1 |

The data in Table 4 indicates the anti-inflammatory efficacy of the compound as per the invention which is applicable over a wide range of cosmetic compositions.

Octopirox® Degradation Under Cool White Light

Cool White Light Treatment:

The cool white light (CWL) irradiation was carried out in an X-Rite (Macbeth) Spectra Light III chamber. CWL mode was chosen which provides stable irradiation mimicking the indoor light. The intensity of light was fixed which estimated at 6 μw/cm2 for UVA and 1.5 μw/cm$^2$ for UVB. The chamber temperature was equal to the room temperature (20±20° C.). The sample was placed in a line close to the center of the chamber. After 24 hours, the sample was analyzed by LCMS (Water UPLC coupled with Quatro Micro MS)., by quantitatively measured using UPLC-UV analysis following DPS derivatization.

The separation was performed by a UPLC BEH C18 column and the mobile phase was acetonitrile/water (60/40, 0.1% formic acid) in isocratic elution. Electrospray ionization in positive mode was applied for MS scan.

It is found that the quantity of Octopirox® is reduced, therefore indicating the degradation of Octopirox® happens under the cool white light. However, there's no compound of formula 1 can be detected in the degradation product. It can be concluded that there's no compound of formula 1 after exposing the Octopirox® under cool white light (indoor light) for long time. The preparation of the compound of formula 1 requires exposure of Octopirox® under strong UV radiation for sufficient time, which differs from the storage condition of Octopirox®.

The invention claimed is:

1. A compound of the formula 1, which may exist in amide form A or enol form B:

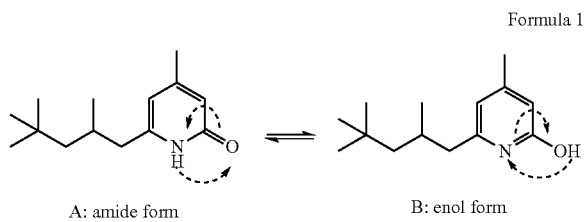 [SMILES: Cc1cc(CC(C)CC(C)(C)C)[nH]c(=O)c1 ; Cc1cc(O)nc(CC(C)CC(C)(C)C)c1]

Formula 1

A: amide form     B: enol form

2. The compound as claimed in claim 1, wherein the compound of formula 1 is in enol form B.

3. A cosmetic composition comprising the compound as claimed in claim 1 and a cosmetically acceptable carrier.

4. The cosmetic composition as claimed in claim 3, wherein amount of said compound is from 0.01 to 10 wt %.

5. The cosmetic composition as claimed in claim 3, wherein said composition is a hair care composition.

6. The hair care composition as claimed in claim 5, wherein said composition is a shampoo, hair conditioner, hair cream, hair gel, hair serum, mousse, or a hair oil.

7. A method of reducing inflammation on a topical surface of a human or an animal comprising a step of applying thereon the composition as claimed in claim 3.

8. A method of treating an inflammatory condition of the skin, or scalp or oral cavity of a human or an animal comprising a step of applying thereon the composition as claimed in claim 3.

9. A process of preparing the compound of the formula 1 as claimed in claim 1 comprising:
   i) preparing a solution of piroctone olamine by dissolving piroctone olamine in an organic solvent or in water comprising at least one surfactant;
   ii) exposing said solution to UV radiation of 100 mW to 2000 mW in a UV chamber for 0.5 hour to 8 hours to cause degradation of piroctone olamine to form degradation products of said piroctone olamine; and
   iii) separating said degradation products of piroctone olamine to a chromatographic technique to get said compound of the formula 1.

10. A non-therapeutic method of reducing inflammation on a topical surface of a human or an animal comprising a step of applying thereon the compound as claimed in claim 1.

11. A method of treating an inflammatory condition of the skin, or scalp or oral cavity of a human or an animal comprising a step of applying thereon the compound as claimed in claim 1.

* * * * *